comprising three wells formed in the underside of said tip portion, one of said wells being on the pitch axis of the blade and the other two being located one fore and one aft of said pitch axis, a cup-shaped liner for each of said wells including a central stud upstanding from the bottom of each liner having external screwthreads at its free end, said stud having a hollow threaded end, a stack of washer-shaped shim weights in each liner which conform closely to the inside diameter of said liners, the inernal diameter of said weights being somewhat greater than the diameter of said studs, means for securing said liners to the bottom and sidewalls of said wells, self-locking nuts engaging said external threads on the free ends of said studs for clamping said weights lightly in stacked position, a cover plate forming a closure for each of said wells and shaped to conform to the airfoil contour of the blade in the vicinity of said wells, and means for securing each of said cover plates in position comprising a screw threaded into the hollow threaded end of each stud.

8. Tip weight attachment means for a composite rotor blade having a tip portion formed essentially of a block of light non-metallic material comprising a well of substantial depth formed in said block in the underside of said tip portion, and a tip weight assembly for balancing the blade located in said well, said assembly including a cylindrical liner adhesively secured to the sidewall of said well, a cover plate forming a closure for said well having a stud projecting into said well, a stack of shim weights in said well having a passage therethrough to receive said stud loosely, said weights having their peripheries closely adjacent said sidewall liner, a nut screw threaded on the end of said stud for clamping said weights lightly in stacked relation, and a screw extended through the top surface of said blade and screw threaded into the end of said stud for securing the assembly in said well.

9. Tip weight attachment means for a rotor blade having a tip portion of lightweight non-metallic material comprising a cylindrical well of substantial depth formed in the under surface of the blade tip portion, and a tip weight assembly for balancing the blade located in the well, said assembly including an annular cup shaped liner for said well having an upstanding central stud which is hollow at its free end, the confronting sidewalls of said liner and said well having screw threads, an internally and externally threaded insert connecting said liner to the cylindrical sidewall of said well, a stack of washer-shaped shim weights in said liner, the external diameter of said weights being substantially equal to the internal diameter of said liner and the internal diameter of said weights being somewhat greater than the diameter of said stud, a self-locking nut threaded on external threads on said stud for lightly clamping said weights, a cover for said well which is shaped to conform to the airfoil contour of the blade in the vicinity of said well, and a screw extended through said cover and threaded into the hollow end of said stud for securing said cover.

10. Tip weight attachment means for a rotor blade having a tip portion of lightweight material comprising a well of substantial depth formed in a major surface of said tip portion, a liner for said well adhesively attached to the side and bottom walls of the well, a stud upstanding from the bottom wall of said liner having external and internal threads at its free end, a stack of shim weights loosely surrounding said stud, said weights having an outside dimension closely fitting said liner, a nut engaging the external threads on said stud for lightly clamping said weights in stacked position, a cover plate having its outer surface shaped to conform to the contour of the blade in the vicinity of said well, and means for securing said cover plate in position including a screw threaded into said internal threads in said stud.

11. The tip weight attachment means of claim 10 in which the well is cylindrical, the liner is annular and cup-shaped and the shim weights are washer-shaped.

12. Tip weight attachment means for a rotor blade having a tip portion formed essentially of a block of lightweight composite material comprising a well formed in said block, a liner adhesively secured in said well having a central stud, a stack of shim weights within said liner surrounding said stud, a cover plate for said well having an outer surface shaped to conform to the airfoil contour of the blade, means for securing said shim weights in stacked position including a nut threaded on exterior threads on the free end of said stud, and a screw extended through said cover plate and threaded into the end of said stud.

13. Tip weight attachment means for a composite rotor blade having a tip portion composed of a block of low density material non-metallic material comprising a tip weight assembly embedded in the material of said block, said assembly including a cup-shaped metallic member having its open end accessible from a major surface of said blade, said member having a centrally located stud therein, a stack of washer-shaped shim weights in said member, a nut threaded on said stud for retaining a selected number of shim weights in stacked position in said member, a cover plate forming a closure for the open end of said member which conforms to the airfoil contour of said blade, and means having a threaded connection with said stud for attaching said plate to said blade.

14. Tip weight attachment means for a composite rotor blade having a tip portion composed of a block of low density material comprising a cup-shaped member embedded in the material of said block with its lip substantially flush with a major surface of said blade, a stack of shim weights in said member having their peripheries closely fitting the inside of said member, means for releasably holding said weights in stacked position in said member, a removable cover for the open end of said member which conforms on its exterior surface to the airfoil contour of the blade and when removed provides access to said weights, and means for securing said cover to said member.

15. The tip weight attachment means of claim 14 in which the means for holding the weights in stacked position is a stud carried by said member which extends through the stacked weights and a nut screw-threaded onto the end of said stud, and the means for securing the cover is a screw extended through the cover and threaded into the end of said stud.

* * * * *

United States Patent [19]
Caulk et al.

[11] 3,999,889
[45] Dec. 28, 1976

[54] MIXING HEAD

[75] Inventors: Robert H. Caulk, Plainfield; Jerry E. Hankins, Newark, both of N.J.

[73] Assignee: Exxon Research and Engineering Company, Linden, N.J.

[22] Filed: Oct. 23, 1975

[21] Appl. No.: 625,072

[52] U.S. Cl. .................................. 416/181; 259/96
[51] Int. Cl.$^2$ ........................................ B01F 7/20
[58] Field of Search .......... 416/181, 199, 178, 187; 259/95, 96, 108, 107

[56] References Cited
UNITED STATES PATENTS

| | | | |
|---|---|---|---|
| 1,383,354 | 7/1921 | Wareing et al. | 416/183 |
| 2,035,333 | 3/1936 | Mills | 416/181 |
| 2,753,162 | 7/1956 | Conley | 416/199 X |
| 2,984,462 | 5/1961 | O'Connor | 416/198 X |
| 3,030,083 | 4/1962 | Stiffler | 416/199 |
| 3,215,409 | 11/1965 | Porciello | 416/181 X |
| 3,606,577 | 9/1971 | Conn | 416/181 |
| 3,630,636 | 12/1971 | Hill | 416/181 X |
| 3,690,621 | 9/1972 | Tanaka | 259/96 |

FOREIGN PATENTS OR APPLICATIONS

| 1,084,243 | 6/1960 | Germany | 416/181 |
|---|---|---|---|

Primary Examiner—Everette A. Powell, Jr.
Attorney, Agent, or Firm—Robert J. Baran

[57] ABSTRACT

The invention relates to a novel mixing head, which comprises a pair of coaxially spaced discs, each of said discs having a plurality of substantially radially extending slots, each of said slots having a leading edge and a trailing edge and each slot being aligned with a corresponding slot on the other disc; a substantially radially extending blade along the trailing edge of each of said aligned slots; and a blade perpendicularly extending substantially from the leading edge of each of said aligned slots to the edge of said discs, said blades being disposed in the space between said discs, perpendicular to the plane of the discs, and are secured to each disc to form compartments in the space between the discs. The novel mixing head also comprises means for connecting with a rotatable shaft. This novel mixer is especially useful for mixing immiscible liquids, to provide high surface areas, and in other processes requiring high local agitation at low power inputs, as for example, in alkylation processes.

5 Claims, 5 Drawing Figures

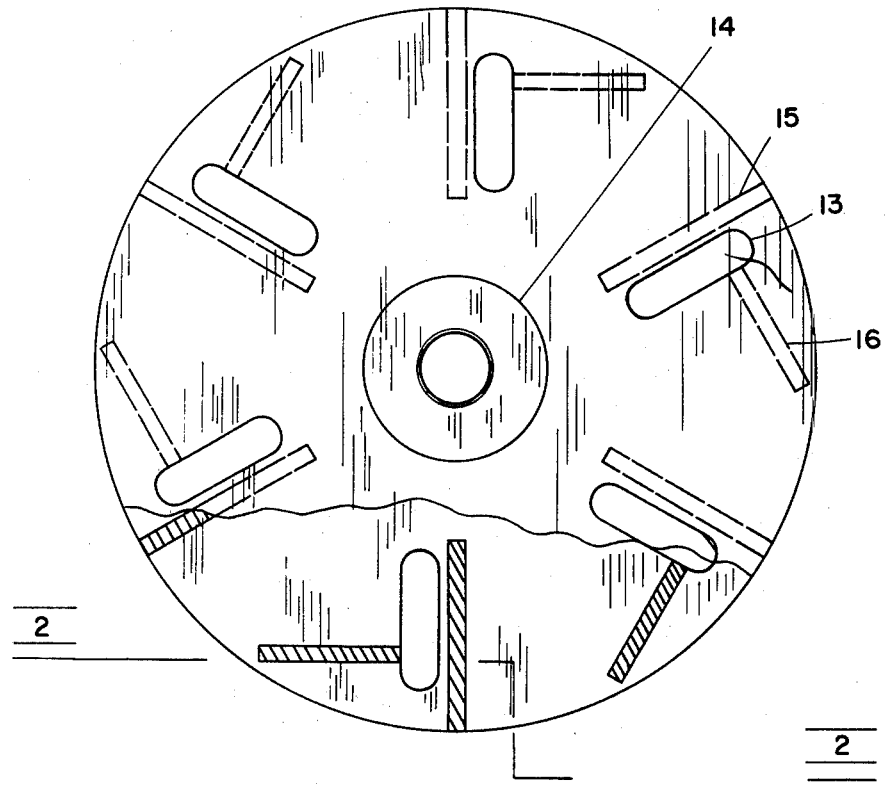

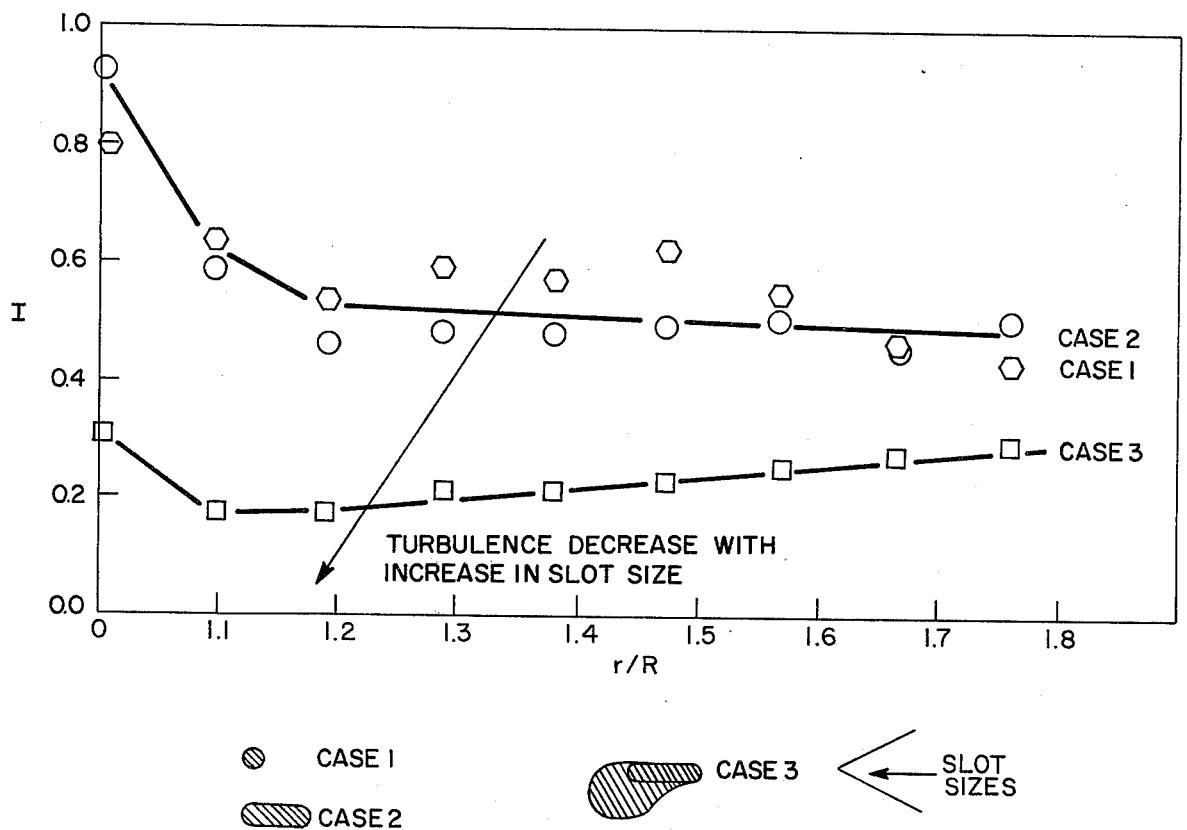
FIGURE 5
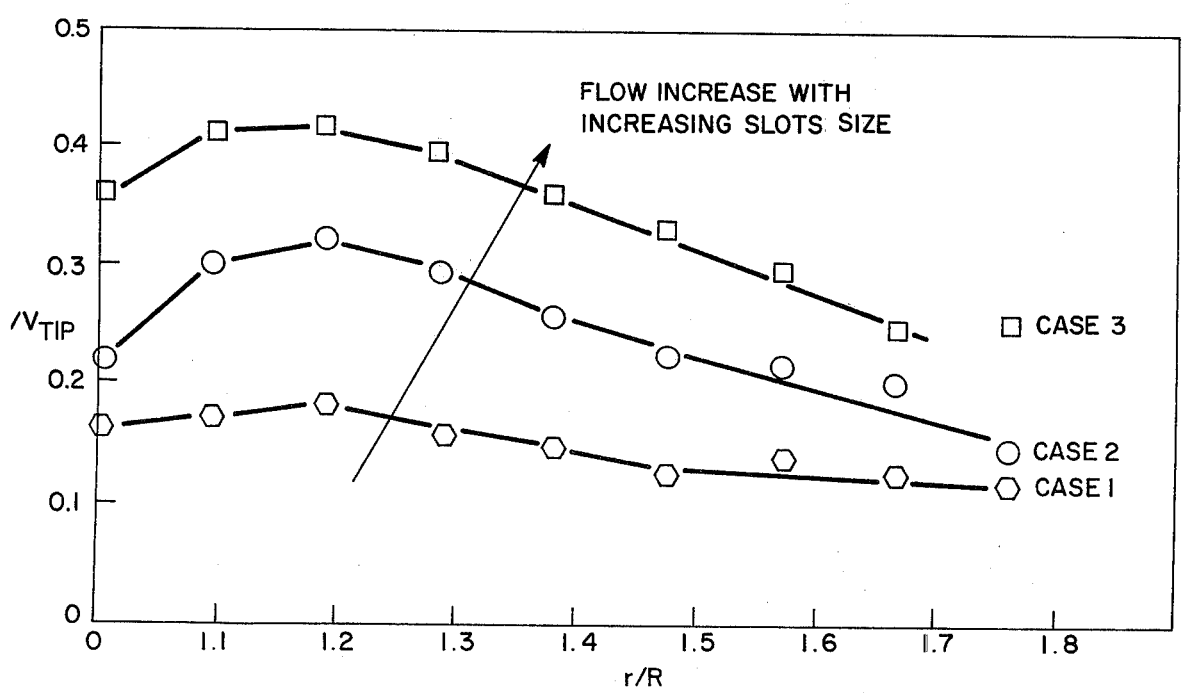

MIXING HEAD

FIELD OF THE INVENTION

This invention relates to a novel mixing head, which comprises a pair of coaxially spaced discs, each of said discs having a plurality of substantially radially extending slots, each of said slots having a leading edge and a trailing edge and each slot being aligned with a corresponding slot on the other disc; a substantially radially extending blade along the trailing edge of each of said aligned slots; and a blade perpendicularly extending substantially from the leading edge of each of said aligned slots to the edge of said discs, said blades being disposed in the space between said discs, perpendicular to the plane of the discs, and are secured to each disc to form compartments in the space between the discs. The novel mixing head also comprises means for connecting with a rotatable shaft. This novel mixer is especially useful for mixing immiscible liquids, to provide high surface areas, and in other processes requiring high local agitation at low power inputs, as for example, in alkylation processes.

BACKGROUND OF THE PRIOR ART

In U.S. Pat. No. 3,215,409, a mixer is disclosed which provides rapid and intense mixing action. This mixer differs from the mixer of the instant invention in both structure and mixing action. The mixer of the instant invention has: (1) no blades exterior to the disc pair; (2) a second blade perpendicular to the radially extending blade; (3) in the preferred embodiment, all blades are connected to both discs to form compartments; and (4) slots in each disc are positioned between the blades pairs and, in said preferred embodiment, of an optimum size. The second blade and optimum slot size are necessary to generate the high value of turbulent intensity accomplished by the instant invention. This structure, of course, fixes the mixing action.

SUMMARY OF THE INVENTION

This invention relates, in general, to a novel mixing head and more specifically to a high shear turbine impeller. It is an object of this invention to provide a novel mixer which is capable of giving higher local turbulence per unit power input than those known in the prior art.

It is a further object of this invention to provide a novel mixer which is effective for use in processes wherein two immiscible liquids must be contacted, for example, in alkylation processes. Further objects of the invention will be apparent from the specification below. The above objects and other features and advantages are attained by a novel mixing head, which includes a pair of coaxially spaced discs, each of said discs having a plurality of substantially radially extending slots, each of said slots having a leading edge and a trailing edge, and each slot being aligned with a slot on the other disc; a substantially radially extending blade along the trailing edge of each of said aligned slots; and a blade perpendicularly extending substantially from the leading edge of each of said aligned slots to the edge of said discs, said blades being disposed in the space between said discs. Preferably, the blade pairs are perpendicular to the plane of the discs and are attached to both discs to define compartments within the space between the coaxial discs. In the most preferred embodiment, the substantially radially extending blade is directly on the radius of the disc and the center line of the substantially radially extending slot extends parallel thereto. This arrangement of said blade and said slot allows for ease of balance of the mixing head. In accordance with this invention, this mixing head may be constructed so as to provide means for attachment to a rotatable shaft. The rotatable shaft is connected to power means so as to rotate the mixing head of this invention. The mixing head of the instant invention preferably comprises at least four, preferably six slots spaced in equidistant relationship around the circumference of the discs.

It has been further discovered that the size of the slots described above must be of a certain dimension to provide the optimum balance of turbulence and flow. For example, as further shown below, the slot will preferably have a length to width ratio of at least 3, more preferably from 3 to 4 and have a length of from 1/8 to 1/12 of the diameter of said discs.

It should be noted that the slot will not be extended further toward the center of the disc, along the radius, then the blade.

The blades which are positioned in the space between the discs are like the slots of equivalent geometry. The mixing head will comprise at least four pairs of said blades, more preferably six, all of which are aligned as disclosed above. The blades will extend substantially from the circumference of the discs along the radius, a distance of from 1/2 to 4/5 of the radius.

The mixer of this invention is especially suitable for processes wherein two immiscible liquids are emulsified. For example, in alkylation processes, such as that described in U.S. Pat. No. 3,470,265, herein incorporated by reference, it is shown that the reaction rates are dependent upon the droplet size of the emulsion formed by the mixing of the isoparaffinolefin (hydrocarbon phase) and sulfuric acid (aqueous phase). It is pointed out in this patent that the creation of high interfacial areas at low mixing energy inputs is very desirable from a commercial standpoint.

BRIEF DESCRIPTION OF THE DRAWINGS

FIG. 5 represents the variations in turbulence and flow experienced with different slot sizes and configurations.

In FIGS. 1 and 2, a preferred embodiment of the novel mixer of the instant invention is shown. FIG. 1 is a top view of the mixer of the instant invention, and FIG. 2 is a side view. Referring to these figures, it is shown that the novel mixer of the instant invention comprises a pair of coaxially spaced discs 10, 11 of substantially equivalent geometry. In each of said discs are a series of radially extending slots 13 and a hollow cylinder 14 is centered through said discs and attached thereto to provide means for attaching the discs to a rotatable shaft. Associated with each of said radially

Figure 1:
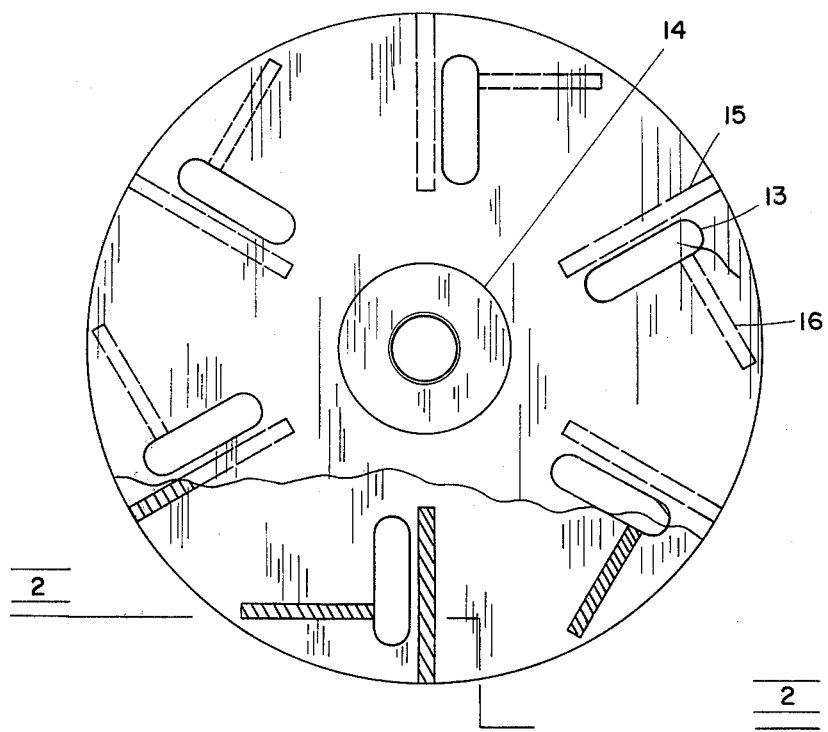
FIG. 1 is a top view of the mixer of the instant invention showing the placement of a series of slots, radially extending blades and perpendicular blades.
Figure 2:
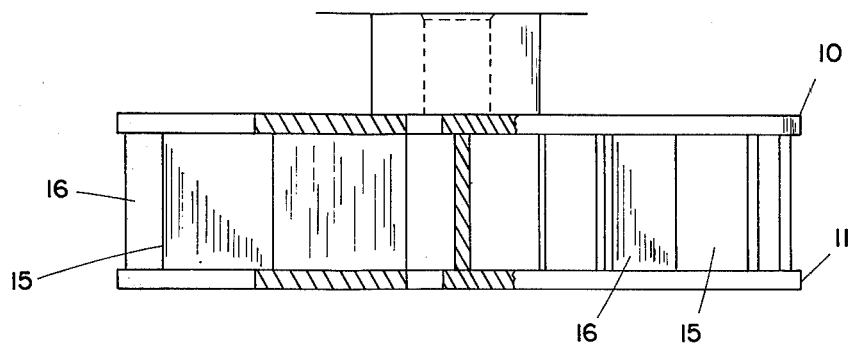
FIG. 2 is a side view of the mixer of the instant invention.
Figure 3:
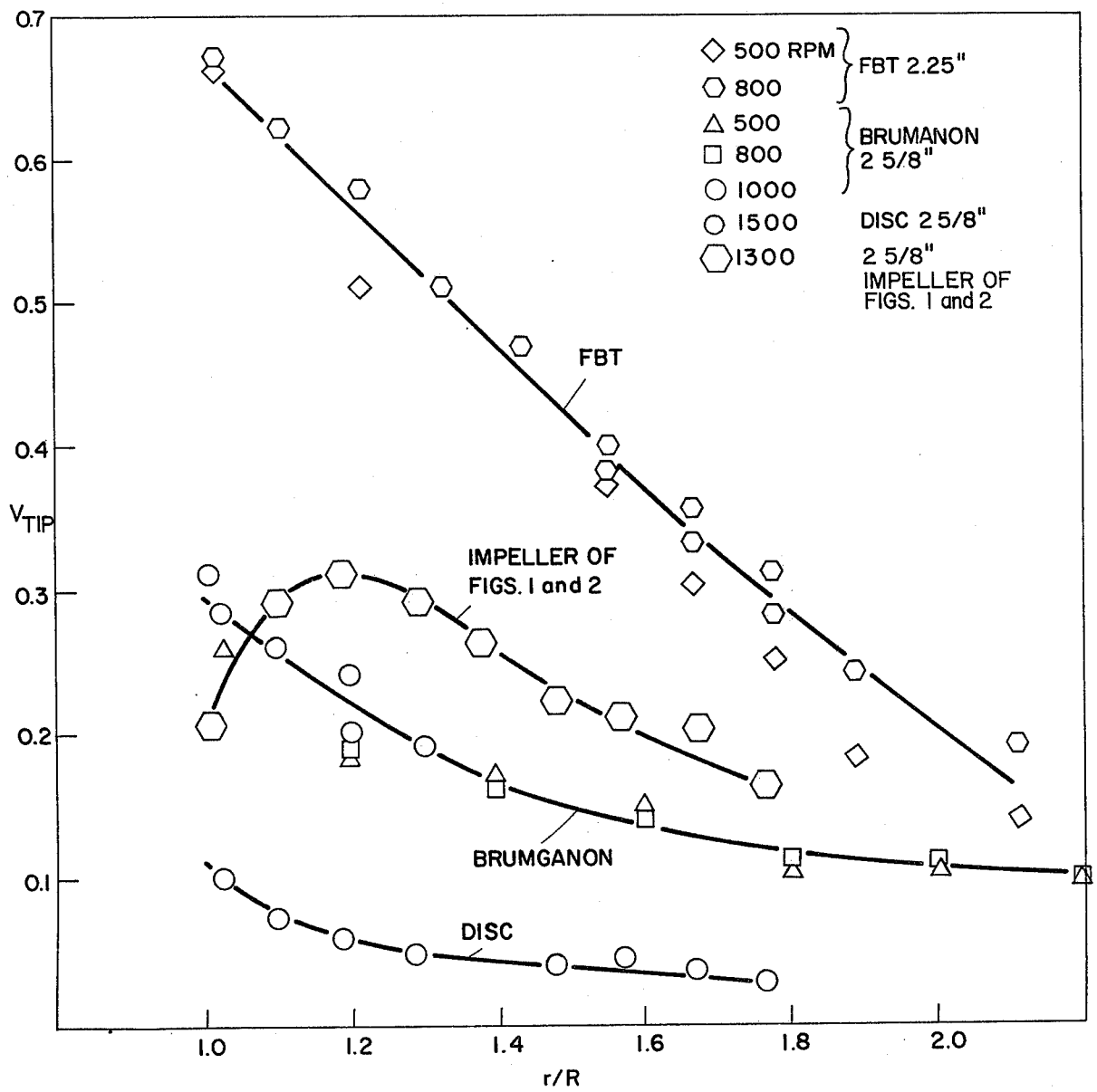
FIG. 3 is a comparison of the performance of the mixer of the instant invention with that of a standard flat blade turbine.
Figure 4:
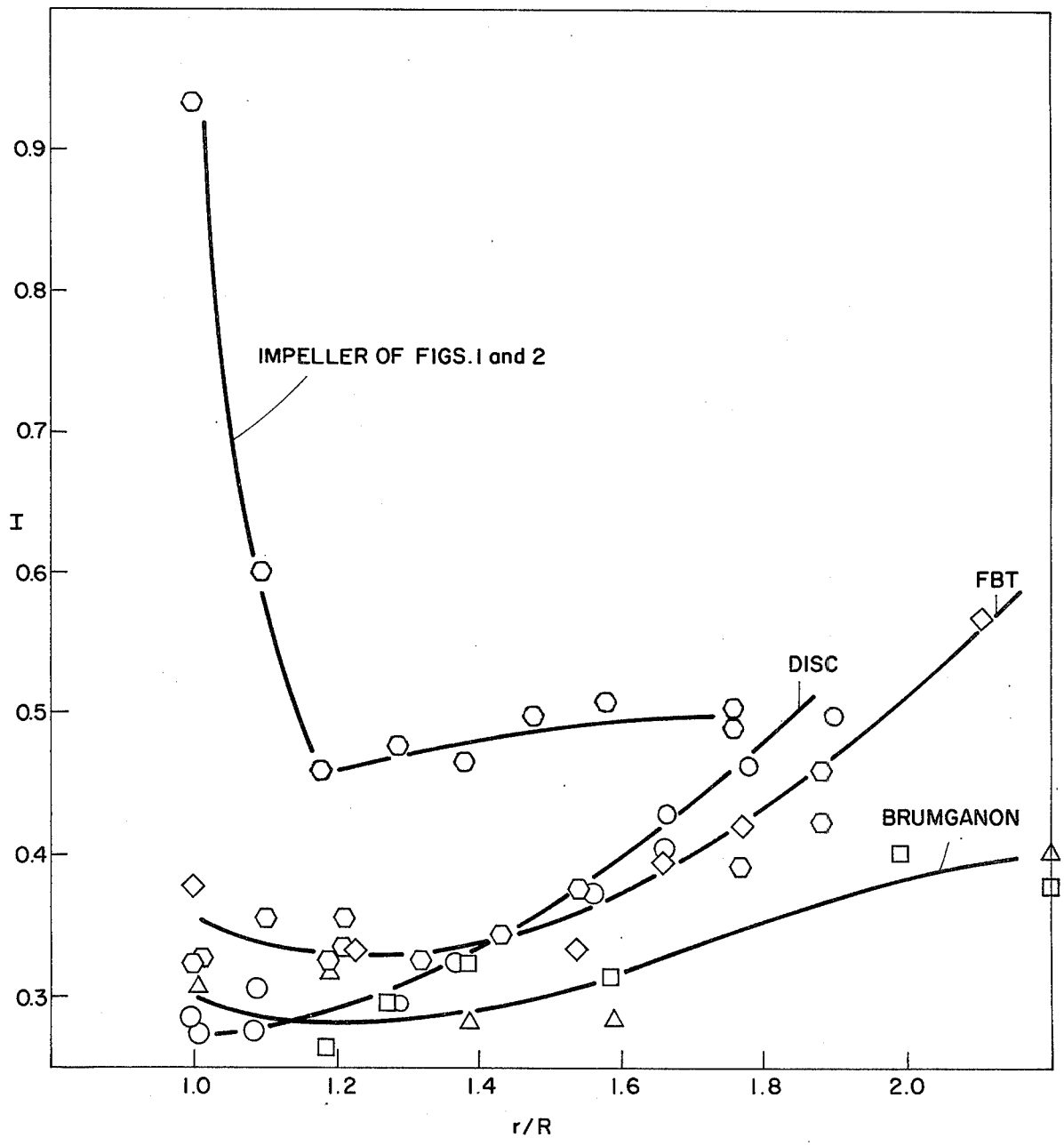
FIG. 4 compares the intensity of the mixer of the instant invention with that of currently available apparatuses.